United States Patent
Nagase et al.

(10) Patent No.: US 11,686,671 B2
(45) Date of Patent: Jun. 27, 2023

(54) CONCENTRATION MEASUREMENT DEVICE

(71) Applicant: FUJIKIN INCORPORATED, Osaka (JP)

(72) Inventors: Masaaki Nagase, Osaka (JP); Hidekazu Ishii, Saka (JP); Kouji Nishino, Osaka (JP); Nobukazu Ikeda, Osaka (JP)

(73) Assignee: FUJIKIN INCORPORATED, Osaka (JP)

( * ) Notice: Subject to any disclaimer, the term of this patent is extended or adjusted under 35 U.S.C. 154(b) by 273 days.

(21) Appl. No.: 17/288,300

(22) PCT Filed: Oct. 18, 2019

(86) PCT No.: PCT/JP2019/041107
§ 371 (c)(1),
(2) Date: Apr. 23, 2021

(87) PCT Pub. No.: WO2020/085236
PCT Pub. Date: Apr. 30, 2020

(65) Prior Publication Data
US 2021/0396657 A1 Dec. 23, 2021

(30) Foreign Application Priority Data

Oct. 26, 2018 (JP) ................. 2018-201838

(51) Int. Cl.
*G01N 21/31* (2006.01)
*G01N 21/85* (2006.01)
(Continued)

(52) U.S. Cl.
CPC ............. *G01N 21/31* (2013.01); *G01N 21/85* (2013.01); *G01N 33/0037* (2013.01);
(Continued)

(58) Field of Classification Search
CPC ... G01N 2021/3133; G01N 2021/1211; G01N 21/31; G01N 33/0037
See application file for complete search history.

(56) References Cited

U.S. PATENT DOCUMENTS

2016/0084700 A1 3/2016 Nagase et al.
2019/0271636 A1 9/2019 Deguchi et al.

FOREIGN PATENT DOCUMENTS

AT 518433 B1 * 10/2017
DE 202017001743 U1 * 6/2017 ............. G01N 21/31
(Continued)

OTHER PUBLICATIONS

International Search Report issued in PCT/JP2019/041107; dated Jan. 7, 2020.

*Primary Examiner* — Maurice C Smith
(74) *Attorney, Agent, or Firm* — Studebaker & Brackett PC

(57) ABSTRACT

A concentration measurement device 100 includes a light source 22 for generating incident light to a measurement space 10A, a photodetector 24 for receiving light emitted from the measurement space, and an arithmetic control circuit 26 for calculating a concentration of a measurement fluid on the basis of an output of the photodetector, and the light source includes a first light-emitting element 22a for generating light having a first wavelength, and a second light-emitting element 22b for generating light having a second wavelength, and the concentration measurement device is configured so as to calculate the concentration using either light of the first wavelength or the second wavelength on the basis of the pressure or temperature of the measurement fluid.

4 Claims, 7 Drawing Sheets

(51) Int. Cl.
*G01N 33/00* (2006.01)
*H01L 21/02* (2006.01)

(52) U.S. Cl.
CPC ........... *G01N 2201/1211* (2013.01); *G01N 2201/1218* (2013.01); *H01L 21/02274* (2013.01)

(56) References Cited

FOREIGN PATENT DOCUMENTS

| JP | 2004138425 A | 5/2004 | |
|---|---|---|---|
| JP | 2011021996 A | 2/2011 | |
| JP | 2013050403 A | 3/2013 | |
| JP | 2014219294 A | 11/2014 | |
| WO | WO-2005100633 A1 * | 10/2005 | ............... B05D 1/60 |
| WO | WO-2012066930 A1 * | 5/2012 | ......... A61B 5/14546 |
| WO | 2016047168 A1 | 3/2016 | |
| WO | 2018021311 A1 | 2/2018 | |

* cited by examiner (a)

(b)

CONCENTRATION MEASUREMENT DEVICE

TECHNICAL FIELD

The present invention relates to a concentration measurement device, more particularly, to a concentration measurement device configured to measure a concentration of a measurement fluid based on an absorbance of light transmitted through a measurement space into which a measurement fluid flows.

BACKGROUND ART

Conventionally, a concentration measurement device for measuring a concentration of a raw material gas formed from a liquid material or a solid material of an organometallic (MO) and supplied to a semiconductor manufacturing equipment is well known. This type of concentration measurement device is configured to measure an absorbance of the transmitted light passing through the measurement cell, by emitting a light with a predetermined wavelength from a light source to be incident through a light incident window to a measurement cell in which a measurement fluid flows and receiving the light by a light-receiving element. The concentration of the measurement fluid can be determined from the measured absorbance, according to Lambert-Beer law (e.g., Patent Document 1 or 2).

PRIOR-ART DOCUMENT

Patent Document

Patent Document 1: Japanese Laid-Open Patent Publication No. 2014-219294
Patent Document 2: International Publication No. WO 2018/021311
Patent Document 3: Japanese Laid-Open Patent Publication No. 2004-138425

SUMMARY OF INVENTION

Technical Problem

In order to measure the concentration of the predetermined fluid contained in the measurement fluid based on the absorbance, it is required to make incident light having a wavelength range in which the absorbance by the predetermined fluid occurs relatively large. When using a light with a wavelength that is hardly absorbed, a difference in concentration of the predetermined fluid can hardly be reflected in absorbance, and the accuracy of concentration detection is remarkably lowered.

However, according to experiments conducted by the present inventors, it is also sometimes difficult to measure the concentration when using a light having a wavelength whose absorbance is too large. For this reason, there has been a problem of appropriately performing the concentration measurement using light having an appropriate wavelength suitable for the measurement fluid.

In view of the above problem, the main object of the present invention is to provide a concentration measurement device capable of appropriately performing concentration measurement on various measurement fluids based on absorbance.

Solution to Problem

A concentration measurement device according to an embodiment of the present invention includes a measurement space in which a measurement fluid flows, a light source for generating incident light to the measurement space, a photodetector for receiving light emitted from the measurement space, and an arithmetic control circuit for calculating a concentration of the measurement fluid on the basis of an output of the photodetector, the arithmetic control circuit being configured to determine the fluid concentration on the basis of a signal of the photodetector according to the Lambert-Beer law, wherein the light source includes a first light-emitting element for generating light having a first wavelength, and a second light-emitting element for generating light having a second wavelength that is different from the first wavelength, and the concentration measurement device is configured to calculate the concentration using either light of the first wavelength or light of the second wavelength on the basis of a pressure or a temperature of the measurement fluid.

In an embodiment, the concentration measurement device further includes a temperature sensor for measuring the fluid temperature in the measurement space and is configured to correct the concentration on the basis of an output of the temperature sensor.

In an embodiment, the concentration measurement device further includes a pressure sensor for measuring the fluid pressure in the measurement space and is configured to correct the concentration on the basis of an output of the pressure sensor.

Effect of Invention

According to the embodiments of the present invention, concentration measurement can be appropriately performed according to the state of the measurement fluid.

DESCRIPTION OF EMBODIMENTS

Embodiments of the present invention will be described below with reference to the drawings, but the present invention is not limited to the following embodiments.

Figure 1:
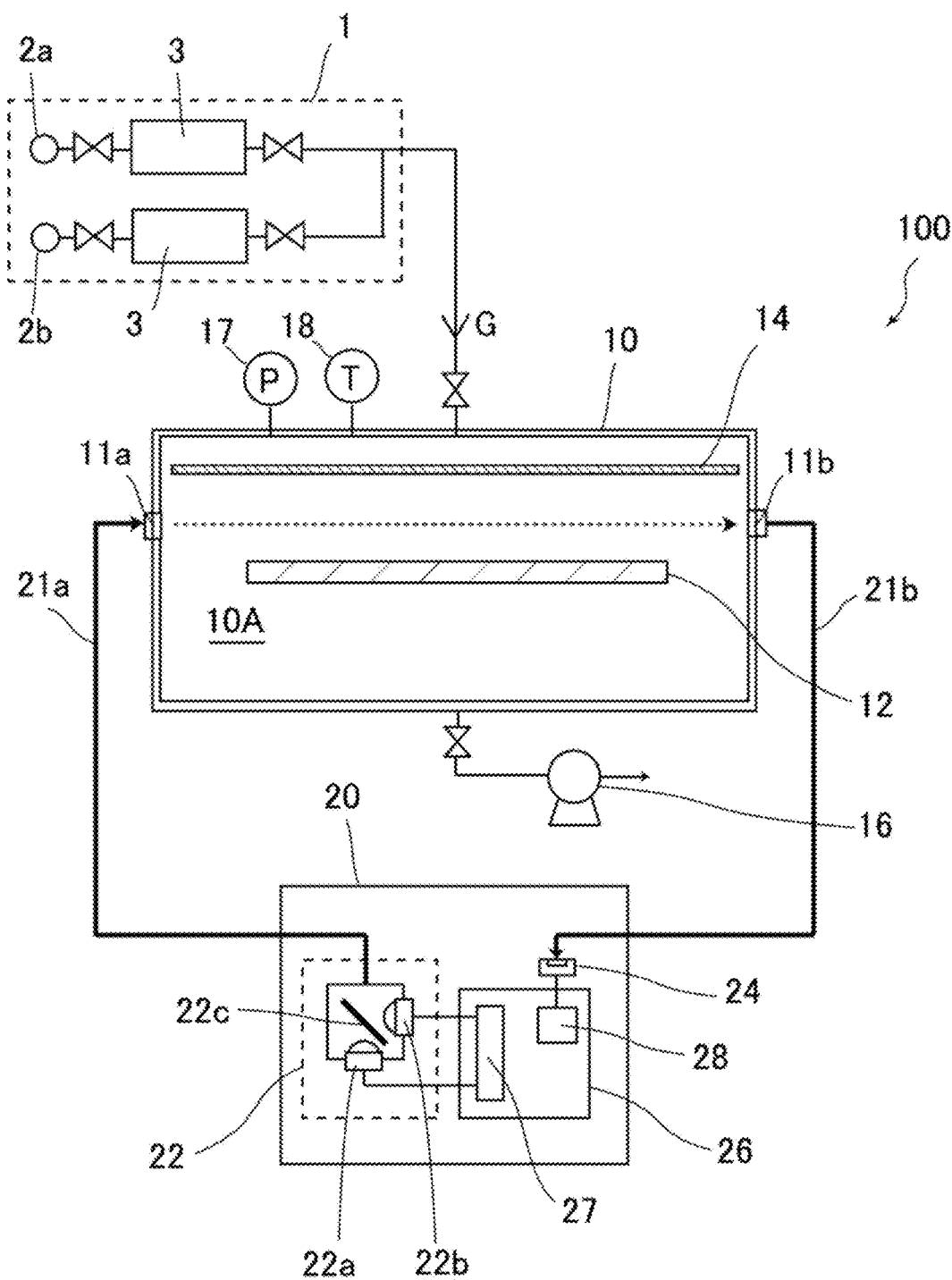
FIG. 1 is a schematic diagram showing an overall configuration of the concentration measurement device according to an embodiment of the present invention.

FIG. 1 is a diagram showing a configuration example of a concentration measurement device 100 according to the present embodiment. The concentration measurement device 100 is configured to measure the concentration of the fluid flowing into the interior (a measurement space 10A) of a chamber 10 of a semiconductor manufacturing equipment (e.g., plasma-enhanced CVD apparatus).

A susceptor 12 for placing a wafer used in a semiconductor device and a shower plate 14 disposed above the susceptor 12 (gas introduction pipe side) are provided inside the chamber 10. The shower plate 14 and the susceptor 12 are arranged in parallel with each other with a predetermined gap therebetween. Moreover, the shower plate 14 is formed with a plurality of holes through which the fluid passes, and the gas introduced into the chamber 10 is diffused by the shower plate 14 to be more uniformly supplied onto the wafer. Further, an exhaust pipe and a vacuum pump 16 are provided below the susceptor 12 in the chamber 10 for exhausting excess gas in the chamber 10. The vacuum pump 16 is also used to evacuate the inside of the chamber 10.

In addition, a pressure sensor 17 and a temperature sensor 18 are attached to the chamber 10 to enable the measurement of the pressure and temperature of the fluid in the chamber 10.

In the present embodiment, a gas supply unit 1 for supplying a gas into the chamber 10 includes a $NO_2$ gas source 2a, and a $N_2$ gas source 2b, each of the gas lines merges in the middle, and it is configured so as to supply a mixed gas G of $NO_2$ and $N_2$ gases into the chamber 10. Further, a flow rate control device 3 is provided in each of the gas lines, and the mixed gas G having a desired mixing ratio (or the concentration of the $NO_2$) can be supplied by adjusting the flow rate of each gas. The flow rate of $NO_2$ gas is set, for example, 3.7 sccm, the flow rate of $N_2$ gas is set, for example, 100 sccm. As the flow rate control device 3, for example, a known pressure type flow rate control device described in Patent Document 3 may be used. The pressure type flow rate control device has a restriction part and a control valve, and is configured to control the flow rate by adjusting the opening degree of the control valve on the basis of an upstream pressure of the restriction part.

The concentration measurement device 100 is configured to measure the concentration of the $NO_2$ in the mixed gas flowing into the measurement space 10A in the chamber 10 on the basis of the absorbance. For this purpose, the concentration measurement device 100 includes an incident-side optical fiber 21a for making light incident to the chamber 10 from one side portion of the chamber 10, an emission-side optical fiber 21b for guiding the light emitted from the other side portion of the chamber 10, and a concentration measurement unit 20 connected to the incident-side optical fiber 21a and the emission-side optical fiber 21b. The concentration measurement unit 20 is provided away from the chamber 10, due to heat-resistant temperature of parts and substrates used therein so that even when the temperature inside of the chamber 10 is high, damage and malfunction do not occur by the influence of the temperature.

In the present specification, the so-called light includes not only visible light but also at least infrared light and ultraviolet light and may include electromagnetic waves of any wavelength. In addition, translucency means that the inner transmittance for the light to be incident to the measurement space 10A is sufficiently high to allow the performance of concentration measurement.

The incident-side optical fiber 21a is connected to one side of the chamber 10, through a light-transmitting incident side window portion 11a provided on the side wall of the chamber 10, to enter the incident light from the concentration measurement unit 20 to the measurement space 10A. Further, the emission-side optical fiber 21b is connected to the other side of the chamber 10 through a light-transmitting emission side window portion 11b provided on the side wall of the chamber 10 to receive the detection light from the measurement space 10A and guide the light to the concentration measurement unit 20.

The incident-side window portion 11a and the emission-side window portion 11b are arranged facing with each other across the measurement space 10A so that the light can pass between the shower plate 14 and the susceptor 12. Further, the concentration measurement device 100 includes a collimator in the vicinity of the incident-side window portion 11a connected to the incident-side optical fiber 21a, and a collimator in the vicinity of the emission-side window portion 11b connected to the emission-side optical fiber 21b, and it is configured so that parallel light can pass the measurement space 10A. The distance between the incident-side window portion 11a and the emission-side window portion 11b, that is, the optical path length of the light passing through the measurement space 10A is set to, for example, 200 mm to 300 mm.

As described above, the concentration measurement unit 20 connected to the chamber 10 through the optical fibers 21a and 21b includes a light source 22 for generating light to be incident to the measurement space 10A, a photodetector 24 for detecting the intensity of light emitted from the measurement space 10A, and an arithmetic control circuit 26 connected to the light source 22 and the photodetector 24. As the light receiving element constituting the photodetector 24, a photodiode or a phototransistor is preferably used, for example.

The light source 22 comprises a first light-emitting element 22a and a second light-emitting element 22b that emit light having different wavelengths, and in this embodiment, the first and second light-emitting elements are LEDs. The first light-emitting element 22a and the second light-emitting element 22b are mounted so as to emit light toward the half mirror 22c, light from either of the light-emitting elements 22a or 22b can be incident to the measurement space 10A through the incident-side optical fiber 21a.

Further, the light source 22 may be configured to output pulsed light of two wavelengths from the first light-emitting element 22a and the second light-emitting element 22b alternately and may be configured to output light of two wavelengths simultaneously. When outputting light of two wavelengths simultaneously, together with combining the light of two wavelengths by a multiplexer of WDM (wavelength division multiplexing method), driving current of different frequencies are flowed into the first light-emitting element 22a and the second light-emitting element 22b using an oscillation circuit. In this manner, by driving each light-emitting element at different frequencies for later frequency analysis (e.g., fast Fourier transform or wavelet transform) performed to a detection signal detected by the photodetector 24, it is possible to measure the intensity and thus the absorbance of the light corresponding to each wavelength component. Further, the light source 22 may be configured to switch between the first light-emitting element 22a and the second light-emitting element 22b at the time when the concentration of the measurement fluid becomes a specific concentration.

The arithmetic control circuit 26 includes a light source control unit 27 connected to the light source 22, and a concentration arithmetic unit 28 connected to the photodetector 24. The light source control unit 27 can control the light emission of the first light-emitting element 22a and the second light-emitting element 22b. The concentration arithmetic unit 28 can calculate the concentration of the measurement fluid based on a detection signal of the photodetector 24.

The arithmetic control circuit 26 is configured of, for example, a processor or a memory provided on a circuit board, and includes a computer program for executing a predetermined arithmetic operation based on an input signal, and can be realized by a combination of hardware and software.

In the concentration measurement device 100 configured as described above, the concentration arithmetic unit 28 of the arithmetic control circuit 26 can obtain the absorbance $A\lambda(-\log_{10}(I/I_0)$ at the wavelength $\lambda$ based on the detection signal from the photodetector 24, and can calculate the gas concentration C based on the Lambert-Beer law shown in the following equation (1):

$$A\lambda = -\log_{10}(I/I_0) = \alpha L C \quad (1)$$

In the above equation (1), $I_0$ is the intensity of the incident light to the measurement space, I is the intensity of light passing through the measurement space, $\alpha$ is the molar absorption coefficient ($m^2/mol$), L is the optical path length (m) in the measurement space, and C is the concentration ($mol/m^3$). The molar absorption coefficient $\alpha$ is a coefficient determined by substances.

The intensity $I_0$ of the incident light in the above equation may be the intensity of light detected by the photodetector 24 when there is no light-absorbing gas in the measurement space 10A, for example, when a purging gas having no light-absorbing property is filled or when it is evacuated.

Details of the light source 22 used for the concentration measurement will be described below. As described above, the light source 22 includes the first light-emitting element 22a and the second light-emitting element 22b. In the present embodiment, the wavelength of the light emitted by the first light-emitting element 22a is 405 nm, and the wavelength of the light emitted by the second light-emitting element 22b is 525 nm. The light source control unit 27 that controls the light source 22 is configured to emit light of either the first light-emitting element 22a or the second light-emitting element 22b, and to allow light of the wavelengths of either 405 nm or 525 nm to be incident to the measurement space 10A. The wavelength of light being used is appropriately selected depending on, for example, the concentration range of the gas to be measured.

Figure 2:
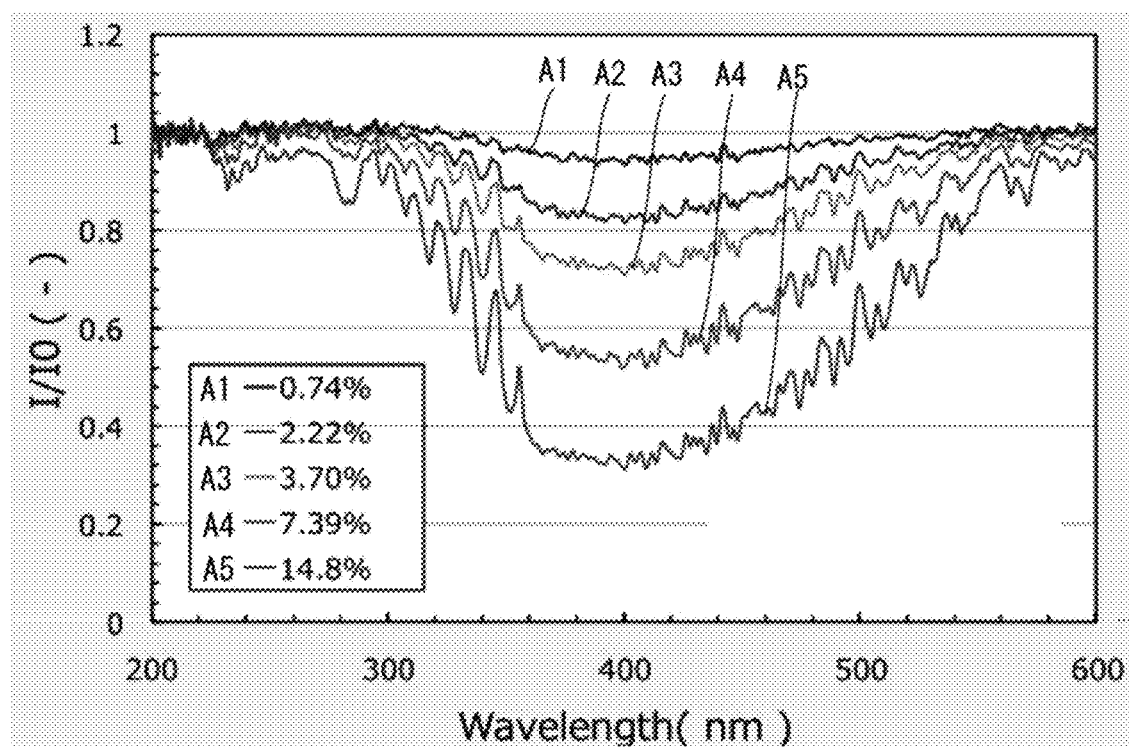
FIG. 2 is a graph showing a difference in the absorption spectrum in accordance with the concentration of the $NO_2$.

FIG. 2 is a graph showing the relationship between the incident light wavelength and the transmittance ($I/I_0$) (hereinafter, sometimes referred to as transmittance characteristics), and showing the difference in transmittance characteristics according to the concentration of $NO_2$ in $N_2$ gas. In the graph, the transmittance characteristics are shown for A1-A5 in the case of $NO_2$ concentrations at 0.74%, 2.22%, 3.70%, 7.39%, and 14.8%, respectively. Note that, when the value of the transmittance is 1, no gas absorbance occurs in the measurement space and the absorbance is 0, and on the other hand, when the value of the transmittance is 0, the gas is completely absorbed in the measurement space, and concentration measurement by the absorbance is impossible. Also, this graph is a graph when the gas pressure in the measurement space is 200 Torr.

It can be seen from FIG. 2 that the peak wavelength of the light absorption by $NO_2$ is present around 405 nm, and the transmittance sufficiently differs in accordance with the concentration in the concentration range of 0.74% to 14.8%, with respect to the light of the wavelength of 405 nm. For this reason, when the concentration of $NO_2$ is in the low concentration range (e.g., 0-20%, particularly 0-15%), it can be seen that concentration measurement can be properly performed from absorbance according to the Lambert-Beer law, by using the light with the wavelength of 405 nm.

However, as can be seen from the graph A5 of the concentration 14.8%, it can be inferred that the transmittance ($I/I_0$) becomes smaller when the concentration becomes relatively larger, and the difference in the concentration is hard to be reflected in the transmittance or the absorbance in the higher concentration region. Therefore, the accuracy of the concentration measurement can be remarkably reduced in the high concentration region. In addition, particularly in a region where the concentration is large, there is a possibility that the concentration measurement cannot be appropriately performed due to a constant value when the transmittance is approximately 0. Therefore, when the measurement in the higher concentration region is performed, the accuracy of the concentration measurement can be improved by using a light shifted from the wavelength (405 nm) having a high absorption coefficient, such as the light of a wavelength (525 nm) that has a low absorption coefficient and is less likely to be absorbed.

For this reason, in the present embodiment in the concentration measurement of $NO_2$, the concentration measurement is performed using light having a wavelength of 380 nm or more and 430 nm or less emitted by the first light-emitting element in the low concentration range, and the concentration measurement is performed using light having a wavelength of 500 nm or more and 550 nm or less emitted by the second light-emitting element in the high concentration range. This makes it possible to extend the range over which concentration measurements can be performed appropriately.

Figure 3:
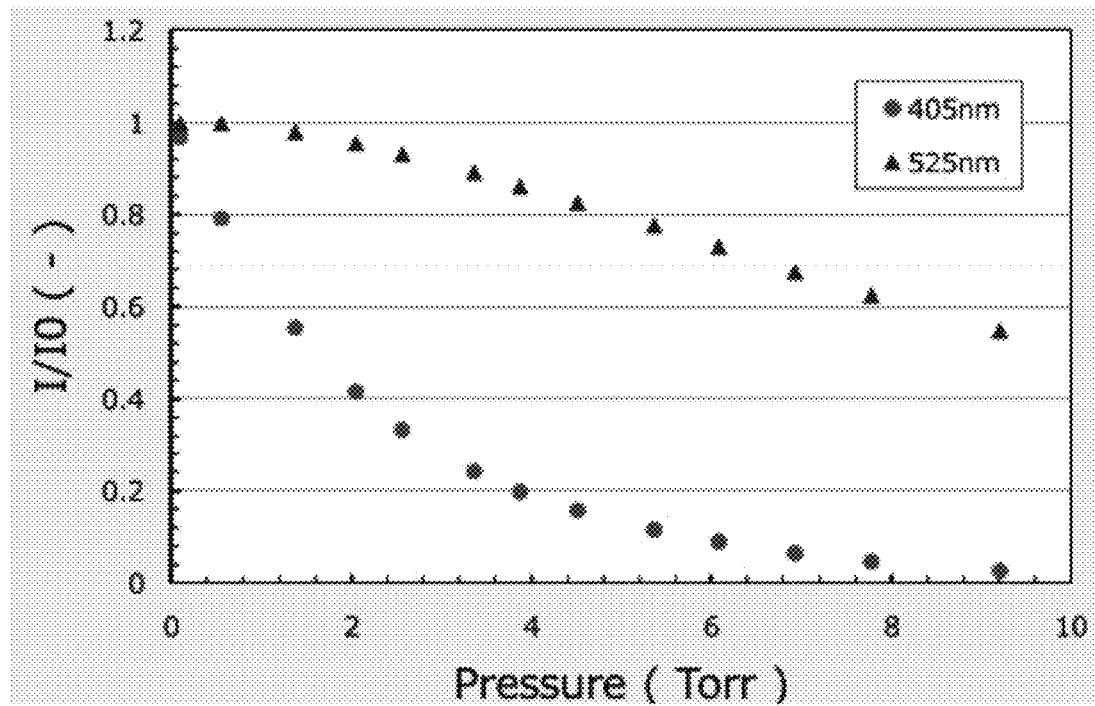
FIG. 3 is a graph showing a measuring result of the $NO_2$ absorbance.
Figure 3:
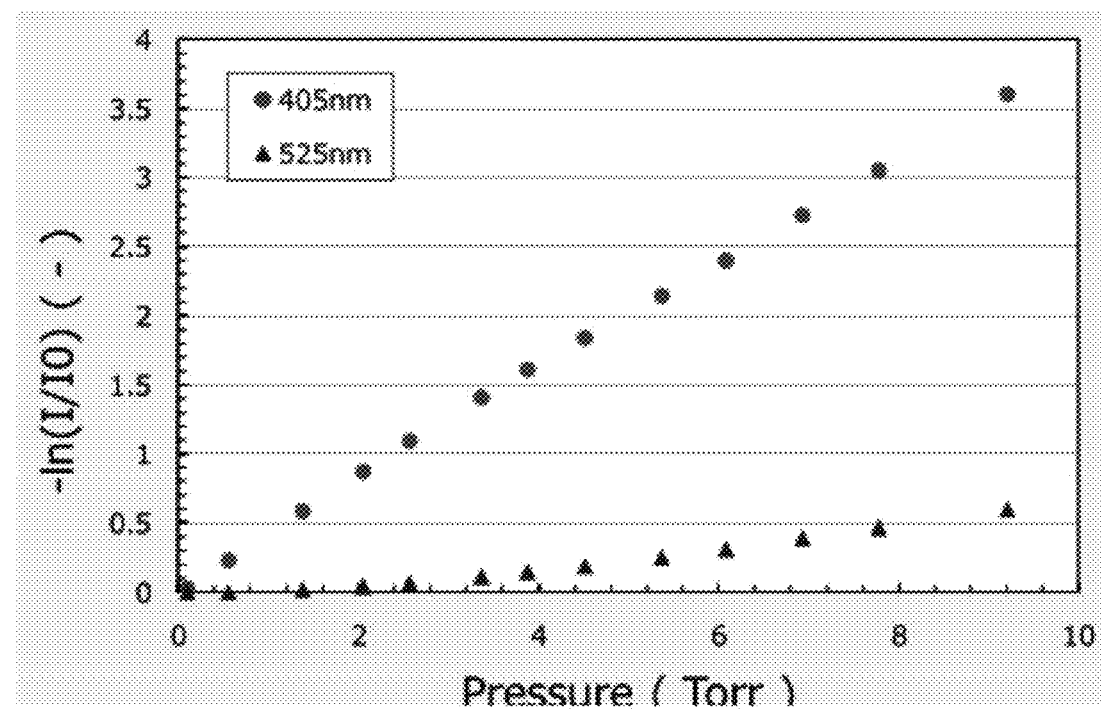

FIGS. 3(a) and 3(b) are graphs showing the relationship between the pressure in the chamber and the transmittance ($I/I_0$) and the relationship between the pressure in the chamber and the absorbance $-\ln(I/I_0)$ when $NO_2$ concentration is 100%, and the wavelengths of the incident light are 405 nm and 525 nm in the respective graphs.

As can be seen from FIG. 3(a), when using light of a wavelength of 405 nm having a high absorption coefficient, since the transmittance can be detected with high accuracy in the first pressure range (e.g., 0 to 6 Torr), the concentration can be suitably measured. However, it can be seen that in the second pressure region (e.g., 6 Torr or more), the detection accuracy of the transmittance is lowered, and the higher the pressure is, the lower the detection accuracy is. Note that, in FIG. 3(b), it is shown that the absorbance can be obtained using light having a wavelength of 405 nm even in the second pressure range, but in practice, since the transmittance becomes almost 0 at a high pressure, it is difficult to accurately determine the absorbance.

On the other hand, when using a light of a wavelength of 525 nm having a lower absorption coefficient, since the transmittance is too high in the first pressure range (that is, the absorbance is too small even at a concentration of 100%), it is difficult to accurately perform the concentration measurement. However, in the second pressure range, since the detection accuracy of the transmittance is good, the concentration detection can also be appropriately performed.

From the above results, it is understood that light having a wavelength of 525 nm is preferable to be used for the concentration measurement when the measurement target is in the high concentration range and the gas pressure is relatively high. Further, it is understood that light having a wavelength of 405 nm is preferably used in the low concentration range, and when the gas pressure is relatively low even in a high concentration range.

The pressure in the chamber that can be actually measured indicates the total pressure Pt of the mixed gas containing the gas component (absorption gas) and the carrier gas to be measured, and when the partial pressure of the gas to be measured is Pm and its concentration is Cm, it can be expressed as Pm=Pt·Cm. It is also possible to derive $\ln(I_0/I)=\alpha_m \cdot L \cdot Pm/RT$ (where $\alpha_m$ is the absorption coefficient of the absorption gas, R is the gas constant of the absorption gas, and T is the gas temperature) from the equation of state of ideal gas and the Lambert-Beer's equation. Further, when the expression is transformed so as to erase the partial pressure Pm from the above equation, $Cm=\ln(I_0/I)-(R \cdot T)/(\alpha_m \cdot L \cdot Pt)$, i.e., the concentration Cm is found to depend on the total pressure Pt and the temperature T.

Therefore, by performing correction based on the chamber pressure (total pressure) Pt and the gas temperature T measured using the pressure sensor 17 and the temperature sensor 18, it is possible to determine the concentration Cm of the absorption gas more accurately. Note that the absorption coefficient $\alpha_m$ of the absorption gas can be obtained in advance by supplying an absorption gas of a specified concentration and measuring the absorbance at the time of shipping or the like, and can be read out from the memory and used at the time of concentration measurement by storing the absorption coefficient $\alpha_m$ in the memory.

Figure 4:
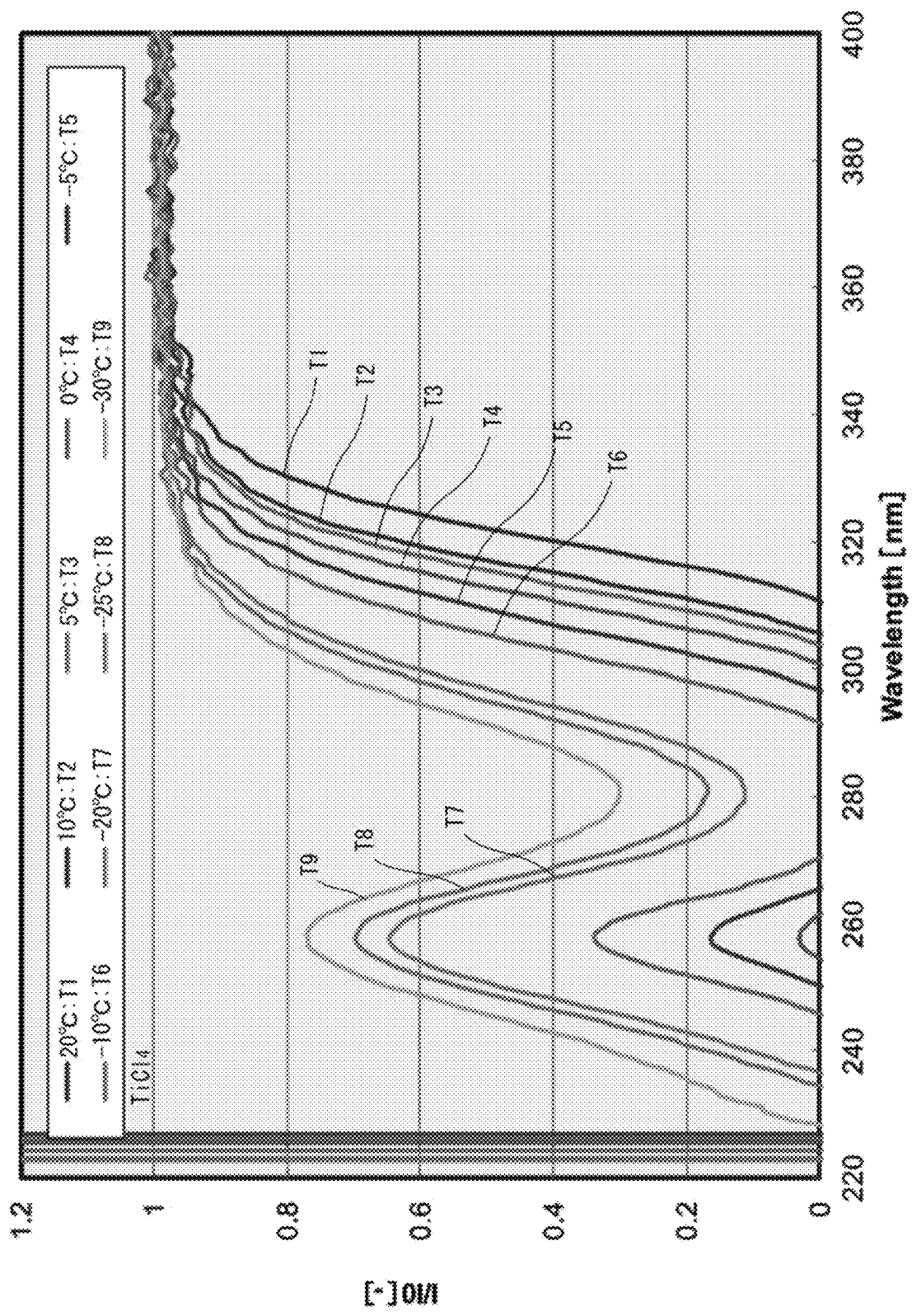
FIG. 4 is a graph showing a difference in the absorption spectrum in accordance with the temperature of the $TiCl_4$.

Next, TiCl$_4$ concentration measurements will be described. FIG. 4 is graphs T1-T9 showing transmittance characteristics at various temperatures (20° C., 10° C., 5° C., 0° C., –5° C., –10° C., –20° C., –25° C., and –30° C.) when TiCl$_4$ concentration is 100%. As can be seen from graphs T1-T9, TiCl$_4$ has absorption peak wavelengths near 230 nm and 285 nm. It can also be seen that the higher the temperature, the greater the degree of absorption at temperatures between –30° C. and 20° C. In particular, as shown in graphs T1 to T6, at temperatures of –10° C. or higher, the transmittance becomes 0 when using light of 280 nm, and it is difficult to measure the concentration in a high concentration region around 100%.

For this reason, it is conceivable to measure the concentration using light having different wavelengths depending on the gas temperature. For example, when measuring the concentration of TiCl$_4$ gas at –20° C. or lower, the concentration may be measured by using light having a wavelength of 280 nm or more and less than 300 nm with a high absorption coefficient, and when measuring the concentration of TiCl$_4$ gas at –20° C. or higher, the concentration may be measured by using light having a wavelength of 300 nm or more and less than 340 nm with a lower absorption coefficient.

Figure 5:
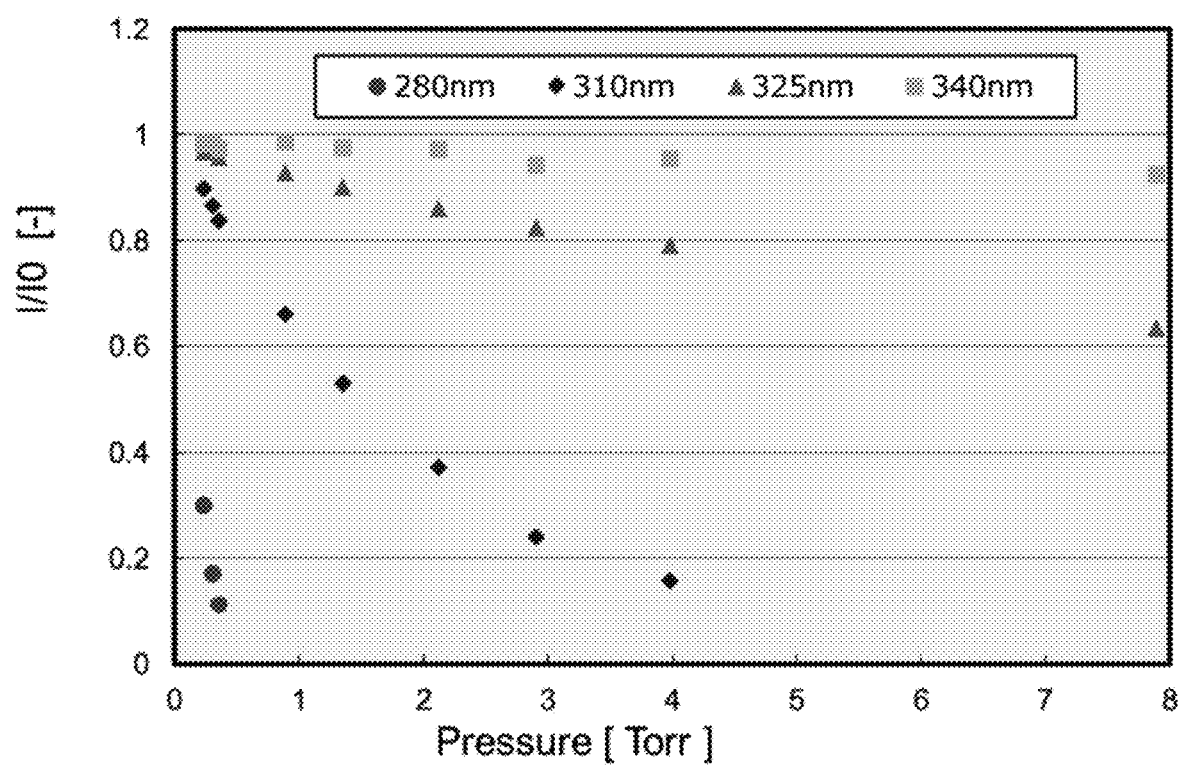
FIG. 5 is a graph showing a measuring result of the $TiCl_4$ absorbance.

FIG. 5 is a graph showing the relation between the pressure in the chamber and the transmittance (I/I$_0$) when TiCl$_4$ concentration is 100%, and the graphs are shown when the wavelengths of the incident light are 280 nm, 310 nm, 325 nm, and 340 nm, respectively.

As can be seen from FIG. 5, when using light of wavelengths from 280 nm to 310 nm having high absorption coefficients, since the transmittance can be detected with high accuracy in the first pressure range (e.g., from 0 nm to 5 Torr), the concentration can be preferably measured. However, it is understood that in the second pressure region (5 Torr or more), the detection accuracy of the transmittance is lowered, and the higher the pressure is, the lower the detection accuracy is. On the other hand, when light having a wavelength from 325 to 340 nm, which has a lower absorption coefficient, the change in transmittance is small in the first pressure range and it is difficult to perform concentration measurement, but the detection accuracy of transmittance is good in the second pressure range, so that concentration detection can be performed appropriately.

From the above results, it is understood that it is preferable to use light having a wavelength of 325 to 340 nm for the concentration measurement at a low temperature and a relatively high gas pressure. It is also found that the use of light having a wavelength of 280 to 310 nm is preferred when the gas pressure is relatively low even at high or low temperatures.

While embodiments of the present invention have been described above, various modifications are possible. For example, although a mode in which incident light of two wavelengths is used is described above using the first light-emitting element and the second light-emitting element, concentration measurement may be performed using light of any of three or more wavelengths using three or more light-emitting elements. For example, when the concentration of NO$_2$ is measured, lights of different wavelengths may be used in the low concentration region, the medium concentration region, and the high concentration region.

In the above description, the concentration measurement device for measuring the gas concentration inside the chamber 10 of the semiconductor manufacturing equipment has been described, but in other embodiments, the concentration measurement device may be an in-line type concentration measurement device. Note that the in-line type reflection type concentration measurement device is disclosed, for example, in Patent Document 2 (WO 2018/021311).

Figure 6:
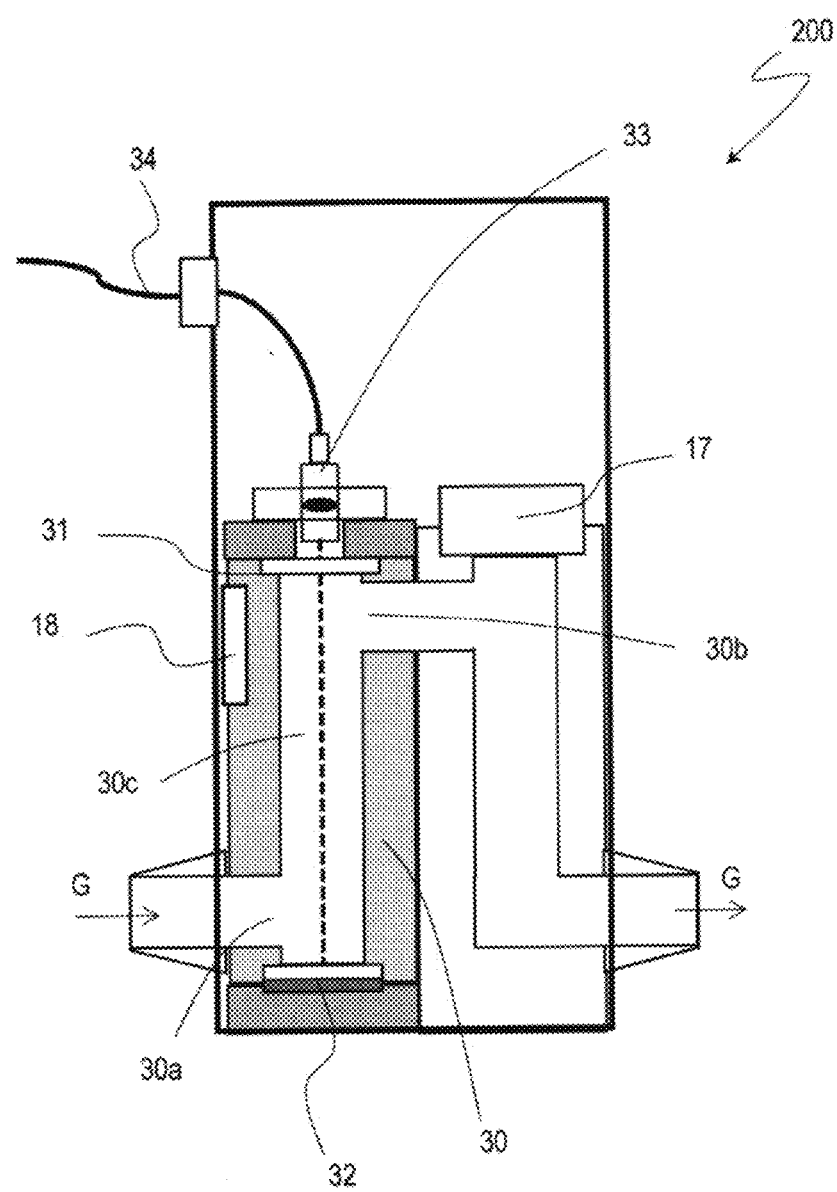
FIG. 6 is a schematic diagram showing an in-line concentration measurement device according to another embodiment of the present invention.

FIG. 6 shows a reflective type measurement cell 30 for use in an in-line reflective concentration measurement device 200. The measurement cell 30 has an inlet 30a, an outlet 30b, and a vertically extending flow path 30c for the mixed gas G, which is the measurement fluid and can be incorporated in the middle of a gas supply line of a semiconductor manufacturing equipment to measure the concentration of the supplied gas. In the present embodiment, the flow path 30c serves as a measurement space for the measurement fluid.

In the measurement cell 30, a translucent window portion (translucent plate) 31 in contact with the flow path 30c and a reflective member 32 for reflecting the incident light are provided. In the vicinity of the window portion 31, a collimator 33 connected to the optical fiber 34 is attached, while making light from a light source (not shown) incident to the measurement cell 30 through the optical fiber 34, it can receive the reflected light from the reflecting member 32, and guide the light to the light detector. Also in the present embodiment, the light source is configured to be capable of generating light of at least two wavelengths, similarly to the concentration measurement device 100 shown in FIG. 1.

The reflective type concentration measurement device 200 also includes a pressure sensor 17 and a temperature sensor 18 for detecting the pressure and temperature of the measurement fluid flowing in the measurement cell 30. Outputs of the pressure sensor 17 and the temperature sensor 18 are connected to the arithmetic unit (not shown) via a sensor cable. Also, the above-described light source, light detector, and the arithmetic unit are provided as a concentration measurement unit at a position away from the measurement cell 30, similarly to the concentration measurement device 100 shown in FIG. 1.

Figure 7:
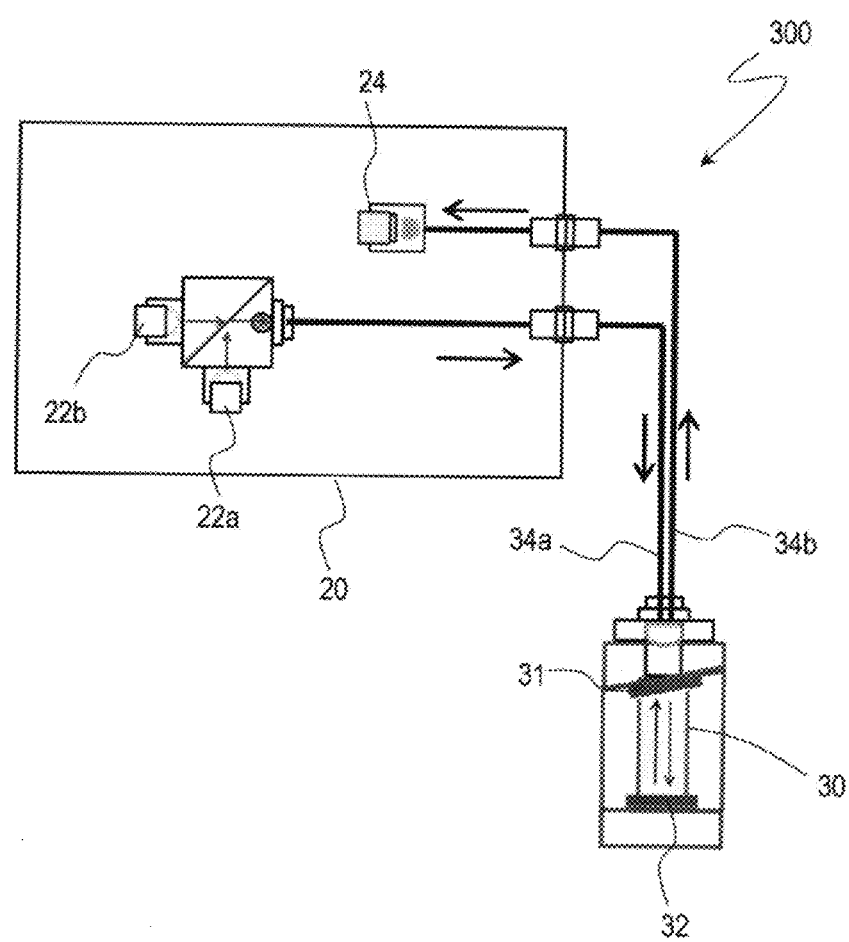
FIG. 7 is a schematic diagram showing an in-line concentration measurement device according to another embodiment of the present invention.

Further, FIG. 7 illustrates a reflection type concentration measurement device 300 of the two-core type in another embodiment, in which the measurement cell 30 and the concentration measurement unit 20 are connected by the incident-side optical fiber 34a and the emission-side optical fiber 34b provided separately. Also in the reflection type concentration measurement device 300, the first light-emitting element 22a and the second light-emitting element 22b having different emission wavelengths are used as the light source, the incident light is incident into the measurement cell 30 through the window portion 31 by the incident side optical fiber 34a. In addition, the reflected light from the reflective member 32 is input to the photodetector 24 through the window portion 31 by the emission side optical fiber 34b. By using separate optical fibers 34a, 34b as same as in the reflective concentration measurement device 300, the effect of stray light can be reduced.

Also in the in-line reflection type concentration measurement devices 200 and 300 described above, by providing light-emitting elements more than two wavelengths in the light source, and appropriately selecting the emission wavelength based on the gas concentration and gas temperature flowing inside the measurement cell (measurement space), it is possible to perform the concentration measurement with improved accuracy over a wider concentration range.

Further, the concentration measurement device according to another embodiment of the present invention may be an in-line concentration measurement device of a transmission type configured to emit incident light from one end side of the measurement cell and take out the measurement light from the other end side of the measurement cell without using a reflecting member.

INDUSTRIAL APPLICABILITY

The concentration measurement device according to the embodiment of the present invention is suitably used for measuring the concentration of the measurement fluid of various conditions.

REFERENCE SIGNS LIST

1 Gas supply unit
2a $NO_2$ Gas source
2b $N_2$ Gas source
3 Flow rate control device
10 Chamber
10A Measurement space
12 Susceptor
14 Shower plate
16 Vacuum pump
17 Pressure sensor
18 Temperature sensor
20 Concentration measurement unit
21a Incident-side optical fiber
21b Emitting-side optical fiber
22 Light source
22a First light-emitting element
22b Second light-emitting element
24 Photodetector
26 Arithmetic control circuit
27 Light source control unit
28 Concentration arithmetic unit
30 Measurement cell
31 Window portion
32 Reflective member

The invention claimed is:

1. A concentration measurement device comprising:
a measurement space into which a measurement fluid flows;
a light source for generating an incident light to the measurement space;
a photodetector for receiving a light emitted from the measurement space; and
an arithmetic control circuit for calculating a concentration of the measurement fluid on the basis of an output of the photodetector, the arithmetic control circuit being configured to determine the concentration on the basis of a signal of the photodetector according to the Lambert-Beer law, wherein
the light source includes a first light-emitting element for generating light having a first wavelength and a second light-emitting element for generating light having a second wavelength that is different from the first wavelength, the concentration measurement device is configured to measure the concentration using the light of either the first wavelength or the second wavelength on the basis of a pressure or a temperature of the measurement fluid.

2. The concentration measurement device according to claim 1, further comprising a temperature sensor for measuring a fluid temperature in the measurement space, wherein the concentration measurement device is configured to correct the concentration on the basis of an output of the temperature sensor.

3. The concentration measurement device according to claim 1, further comprising a pressure sensor for measuring a fluid pressure in the measurement space, wherein the concentration measurement device is configured to correct the concentration on the basis of an output of the pressure sensor.

4. The concentration measurement device according to claim 2, further comprising a pressure sensor for measuring a fluid pressure in the measurement space, wherein the concentration measurement device is configured to correct the concentration on the basis of an output of the pressure sensor.

* * * * *